(12) United States Patent
Flom et al.

(10) Patent No.: US 11,234,715 B2
(45) Date of Patent: Feb. 1, 2022

(54) METHOD AND APPARATUS FOR PROVIDING ARTHROSCOPIC MICROFRACTURE THERAPY

(71) Applicant: Stryker Corporation, Kalamazoo, MI (US)

(72) Inventors: James Flom, Redwood City, CA (US); Julian Nikolchev, Portola Valley, CA (US)

(73) Assignee: Stryker Corporation, Kalamazoo, MI (US)

( * ) Notice: Subject to any disclaimer, the term of this patent is extended or adjusted under 35 U.S.C. 154(b) by 25 days.

(21) Appl. No.: 16/285,574

(22) Filed: Feb. 26, 2019

(65) Prior Publication Data
US 2019/0254687 A1 Aug. 22, 2019

Related U.S. Application Data

(63) Continuation of application No. 14/289,159, filed on May 28, 2014, now Pat. No. 10,213,216.

(60) Provisional application No. 61/827,910, filed on May 28, 2013, provisional application No. 61/919,337, filed on Dec. 20, 2013.

(51) Int. Cl.
*A61B 17/16* (2006.01)
*A61B 17/17* (2006.01)

(52) U.S. Cl.
CPC ...... *A61B 17/1666* (2013.01); *A61B 17/1746* (2013.01); *A61B 17/1796* (2013.01); *A61B 17/1631* (2013.01)

(58) Field of Classification Search
CPC ............ A61B 17/1666; A61B 17/1675; A61B 17/1746; A61B 17/1764; A61B 17/1796
USPC ................................ 606/81, 87–89, 144–148
See application file for complete search history.

(56) References Cited

U.S. PATENT DOCUMENTS

| | | | |
|---|---|---|---|
| 4,744,353 A | 5/1988 | McFarland | |
| 5,637,112 A | 6/1997 | Moore et al. | |
| 8,409,230 B2 | 4/2013 | Pamichev et al. | |
| 9,241,720 B2* | 1/2016 | Forsell | A61F 2/4607 |
| 2009/0012526 A1 | 1/2009 | Fletcher | |
| 2010/0203155 A1 | 8/2010 | Wei et al. | |
| 2010/0292731 A1 | 11/2010 | Gittings et al. | |
| 2012/0022541 A1* | 1/2012 | McKay | A61B 17/8805 |
| | | | 606/94 |
| 2013/0296864 A1 | 11/2013 | Burley et al. | |
| 2014/0012292 A1 | 1/2014 | Stewart et al. | |
| 2014/0228848 A1* | 8/2014 | Torrie | A61B 17/1703 |
| | | | 606/80 |

* cited by examiner

*Primary Examiner* — Si Ming Ku
(74) *Attorney, Agent, or Firm* — Pandiscio & Pandiscio

(57) ABSTRACT

A method for providing therapy to a patient, the method comprising:
providing microfracture therapy to the acetabular cup of the patient, wherein providing microfracture therapy to the acetabular cup of the patient comprises forming at least one hole extending from the acetabular shelf to the cortical bone bed of the acetabular cup, such that blood may flow from the cancellous bone underlying the cortical bone bed to the surface of the cortical bone bed, whereby to form a blood clot at the surface of the cortical bone bed.

29 Claims, 22 Drawing Sheets

METHOD AND APPARATUS FOR PROVIDING ARTHROSCOPIC MICROFRACTURE THERAPY

REFERENCE TO PENDING PRIOR PATENT APPLICATIONS

This patent application is a continuation of pending prior U.S. patent application Ser. No. 14/289,159, filed May 28, 2014 by Pivot Medical, Inc. for METHOD AND APPARATUS FOR PROVIDING ARTHROSCOPIC MICROFRACTURE THERAPY, which in turn claims benefit of:

(i) prior U.S. Provisional Patent Application Ser. No. 61/827,910, filed May 28, 2013 by Pivot Medical, Inc. and Julian Nikolchev et al. for METHOD AND APPARATUS FOR PROVIDING ARTHROSCOPIC MICROFRACTURE THERAPY; and (ii) prior U.S. Provisional Patent Application Ser. No. 61/919,337, filed Dec. 20, 2013 by Pivot Medical, Inc. and James Flom et al. for METHOD AND APPARATUS FOR PROVIDING ARTHROSCOPIC MICROFRACTURE THERAPY.

The three (3) above-identified patent applications are hereby incorporated herein by reference.

FIELD OF THE INVENTION

This invention relates to methods and apparatus for providing medical therapy in general, and more particularly to methods and apparatus for providing arthroscopic microfracture therapy.

BACKGROUND OF THE INVENTION

Articular cartilage is a smooth, resilient tissue which covers the opposing ends of bones and facilitates the smooth movement of the bones relative to one another. However, when articular cartilage is damaged (e.g., through injury or prolonged wear), subsequent motion of the bones tends to increase that damage, ultimately causing the cartilage to wear away completely. When this occurs, the bones rub directly against one another, typically resulting in substantial pain for the patient and reduced mobility of the joint. In many cases, such damage to articular cartilage can lead to osteoarthritis.

Microfracture therapy is an orthopedic procedure which can help to restore articular cartilage. More particularly, microfracture therapy creates tiny fractures in the cortical bone bed disposed immediately below the damaged articular cartilage. In cases where the native cartilage has been damaged beyond repair or has been surgically removed, microfracture therapy can be applied to the exposed cortical bone bed. These micro fractures permit blood to seep out of the underlying cancellous bone to the surface of the cortical bone bed and essentially create blood clots which release cartilage-building cells. These cartilage-building cells then result in the formation of replacement hyaline-like cartilage, fibrous tissue and/or fibrocartilage.

In addition to the foregoing, microfracture therapy can also be used to enhance the attachment (or re-attachment) of soft tissue to bone, e.g., to attach (or re-attach) a ligament to bone or to attach (or re-attach) a labrum, labral/chondral junction (i.e., the "transition zone" between cartilage and the labrum) or cartilage to bone. In this situation, the microfracture therapy creates tiny fractures in the cortical bone bed disposed immediately below the location where the soft tissue is to be attached to (or re-attached to) the bone, thereby permitting blood to seep out of the underlying cancellous bone, essentially creating blood clots between the soft tissue and the bone which release restorative cells at the surgical site.

To date, microfracture therapy is generally performed using a small, sharp pick or awl to create the small microfracture holes in the cortical bone bed. However, such picks or awls are generally used by driving them longitudinally, e.g., with a hammer or mallet, thereby requiring substantially direct linear access to the bone surface which is to receive the microfracture therapy. Furthermore, where the microfracture must be created in a bone surface which is not substantially aligned with the angle of access, it can be difficult to generate the forces required for the pick or awl to penetrate the hard cortical bone and release blood from the underlying cancellous bone.

In many cases, e.g., for certain sites on the lower femur, such direct linear access to the microfracture site may be readily available. However, in other cases, intervening anatomical structures can make it difficult or impossible to obtain direct linear access to the microfracture site, and hence can make it difficult or impossible to use a conventional pick or awl to provide microfracture therapy to the bone. This is particularly true where the microfracture surgery is to be performed arthroscopically. By way of example but not limitation, it can be difficult or impossible to arthroscopically provide microfracture therapy to the acetabular cup of the hip using a conventional pick or awl, given the anatomical constraints typically imposed in arthroscopic hip surgery.

The present invention is intended to provide a novel method and apparatus for providing arthroscopic microfracture therapy, particularly in locations where it is difficult or impossible to utilize a conventional pick or awl in the microfracture therapy.

The present invention is also intended to provide a novel method and apparatus for securing soft tissue to bone.

SUMMARY OF THE INVENTION

The present invention provides a novel method and apparatus for providing arthroscopic microfracture therapy, particularly in locations where it is difficult or impossible to utilize a conventional pick or awl in the microfracture therapy.

The present invention also provides a novel method and apparatus for securing soft tissue to bone.

In one preferred form of the invention, there is provided, a method for providing therapy to a patient, the method comprising:

providing microfracture therapy to the acetabular cup of the patient, wherein providing microfracture therapy to the acetabular cup of the patient comprises forming at least one hole extending from the acetabular shelf to the cortical bone bed of the acetabular cup, such that blood may flow from the cancellous bone underlying the cortical bone bed to the surface of the cortical bone bed, whereby to form a blood clot at the surface of the cortical bone bed.

In another preferred form of the invention, there is provided, a method for attaching soft tissue to bone, the method comprising:

forming at least one hole extending from a first side of the bone to a second side of the bone, wherein the second side of the bone comprises a cortical bone bed which is to receive the soft tissue, such that blood may flow from the cancellous bone underlying the cortical bone bed to the surface of the cortical bone bed, whereby to form a blood clot at the surface of the cortical bone bed; and attaching the soft tissue to the second side of the bone at the cortical bone bed.

In another preferred form of the invention, there is provided, apparatus for providing microfracture therapy to the acetabular cup of a patient, the apparatus comprising:

a drill guide comprising a distal end through which a drill bit may be passed; and an aiming guide attached to the drill guide and having a distal end aligned with, but spaced from, the distal end of the drill guide;

wherein the distal end of the drill guide is spaced from the distal end of the aiming guide by a distance large enough to accommodate the portion of the acetabular cup which is to receive the microfracture therapy and the soft tissue adjacent to the portion of the acetabular cup which is to receive the microfracture therapy.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

The present invention provides a novel method and apparatus for providing arthroscopic microfracture therapy. The novel apparatus permits microfracture therapy to be applied to a bone surface even where that bone surface is set at an angle to the axis of approach and/or where it might otherwise be difficult or impossible to use a conventional pick or awl to provide the microfracture therapy.

The present invention also provides a novel method and apparatus for securing soft tissue to bone.

The present invention will hereinafter be discussed in the context of re-attaching a detached labrum, detached cartilage and/or detached labral/chondral junction to the rim of the acetabular cup, with such re-attachment being accomplished with the provision of microfracture therapy and with minimal interference with the articular surfaces of the hip joint. It should be appreciated, however, that the present invention may also be provided as "stand-alone" microfracture therapy (i.e., not combined with soft tissue re-attachment) and/or the present invention may be used in other joints and/or on other bone surfaces.

Figure 1:
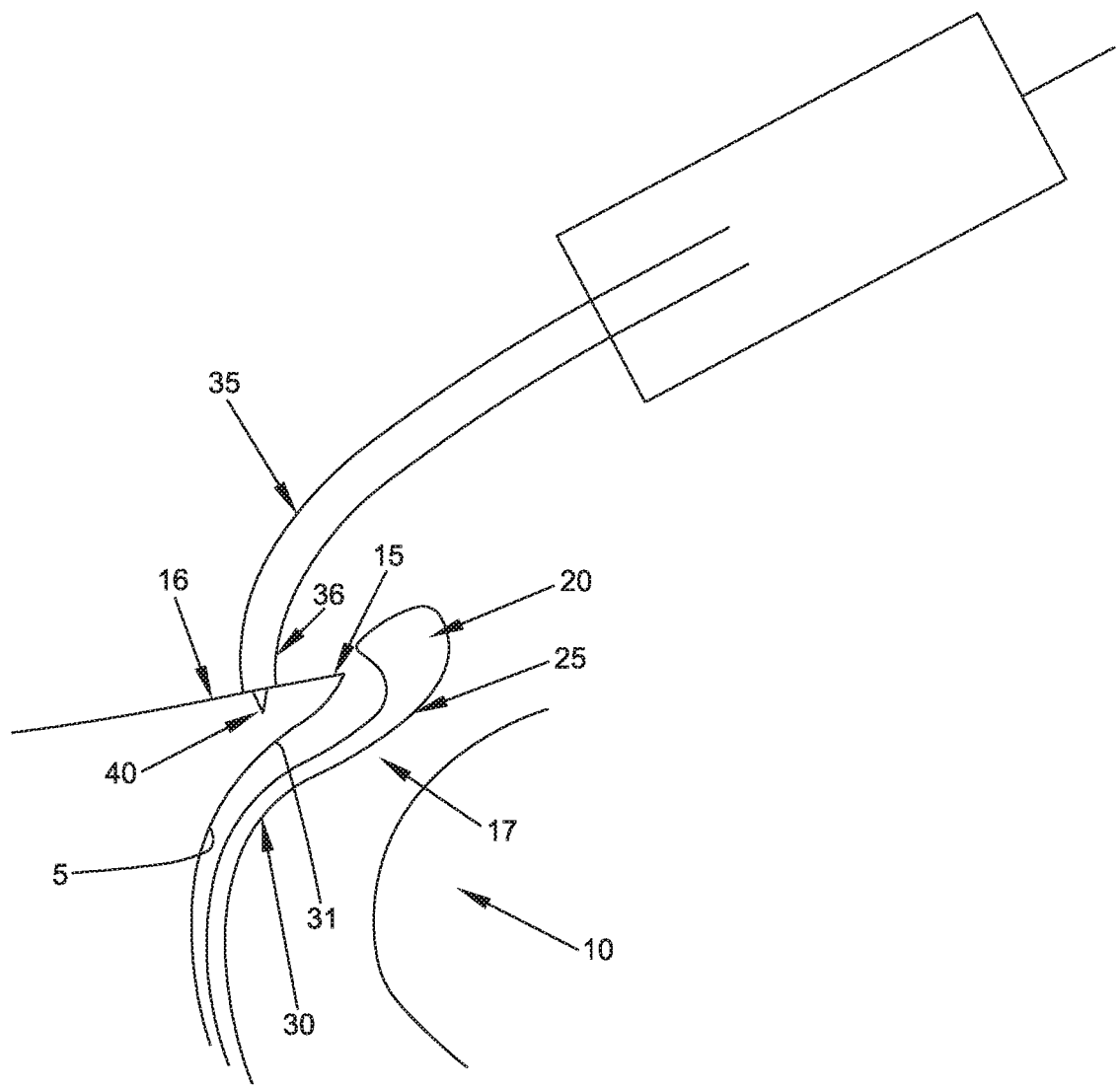
FIGS. 1-7 are schematic views showing a novel approach for providing microfracture therapy to the rim of the acetabular cup and for re-attaching soft tissue to the acetabular cup.
Figure 2:
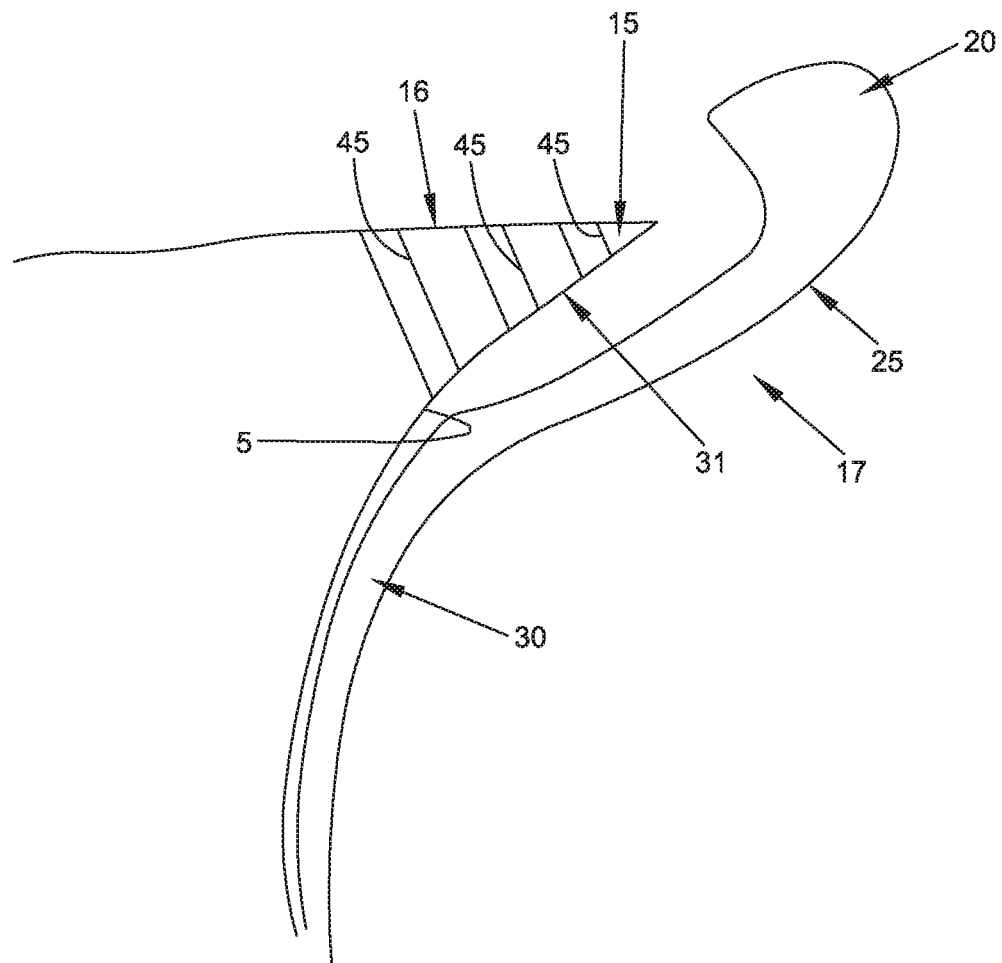

Looking first at FIG. 1, there is shown an acetabular cup 5 and a femoral head 10. Acetabular cup 5 is characterized by a rim 15 and an acetabular shelf 16. Also shown is detached tissue 17 (e.g., labrum 20, labral/chondral junction 25 and/or cartilage 30) spaced from rim 15 of acetabular cup 5, whereby to expose cortical bone bed 31. In accordance with the present invention, a curved drill guide 35 having a distal end 36 is used to position a flexible drill bit 40 against the outside surface of rim 15 of acetabular cup 5 (i.e., against acetabular shelf 16 of acetabular cup 5), such that flexible drill bit 40 may form a hole 45 through rim 15 of acetabular cup 5 in an "outside-in" manner (i.e., from acetabular shelf 16 to cortical bone bed 31). See FIG. 2. This action allows blood to be released, via hole 45, from the underlying cancellous bone to cortical bone bed 31 (against which detached tissue 17 will be re-attached).

If desired, curved drill guide 35 may be of the sort disclosed in U.S. Patent Publication No. US 2013/0296864, which patent application is hereby incorporated herein by reference. Alternatively, other curved drill guides of the sort well known in the art may be used.

If desired, flexible drill bit 40 may be of the sort disclosed in the aforementioned U.S. Patent Publication No. US 2013/0296864. Alternatively, other flexible drill bits of the sort well known in the art may be used.

The foregoing process is then preferably repeated a number of times so as to provide a plurality of holes 45 extending through rim 15 of acetabular cup 5 (i.e., from acetabular shelf 16 to cortical bone bed 31), whereby to provide robust microfracture therapy to cortical bone bed 31 (against which detached tissue 17 is to be re-attached).

Figure 3:
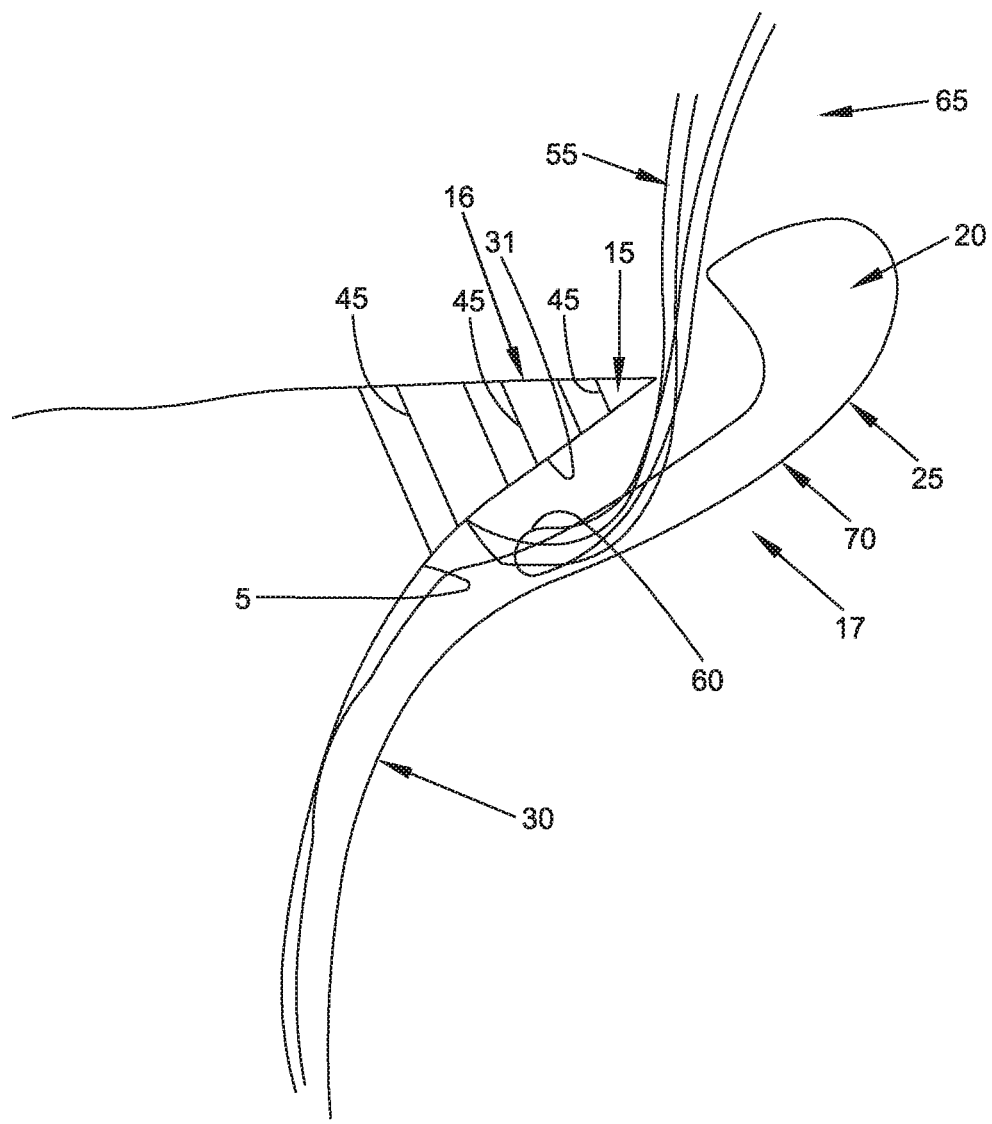
Figure 4:
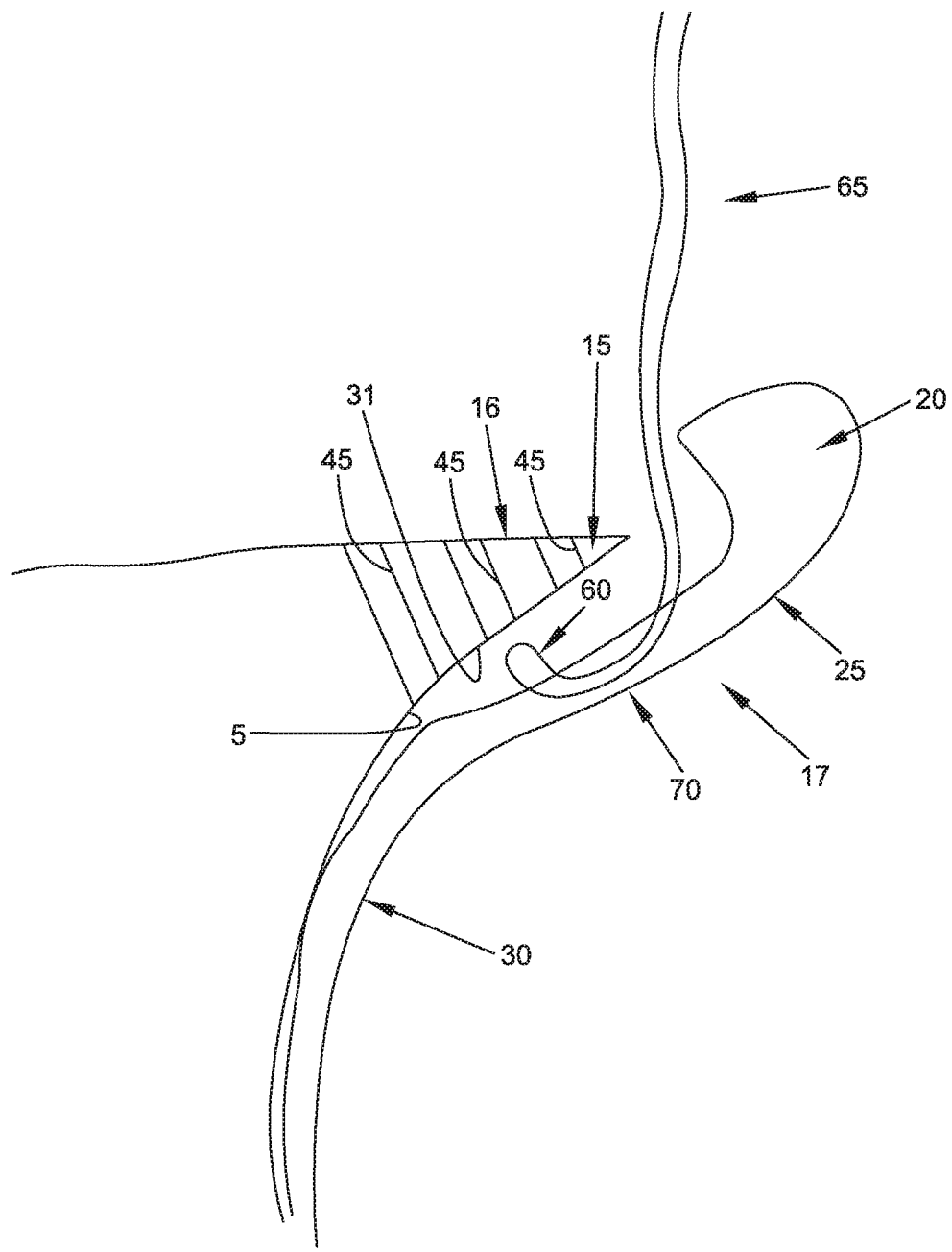

Next, and looking now at FIG. 3, a suture passer 55 is used to pass a loop 60 of suture 65 through detached tissue 17, whereby to present loop 60 of suture 65 adjacent to the mouth of a hole 45 (see FIG. 4). Preferably loop 60 of suture 65 is passed through detached tissue 17 so that suture 65 does not extend through the articular side 70 of detached tissue 17.

If desired, the suture passer may be of the sort disclosed in U.S. Patent Publication No. 2014/0012292, which patent application is hereby incorporated herein by reference. Alternatively, other suture passers of the sort well known in the art may be used.

Figure 5:
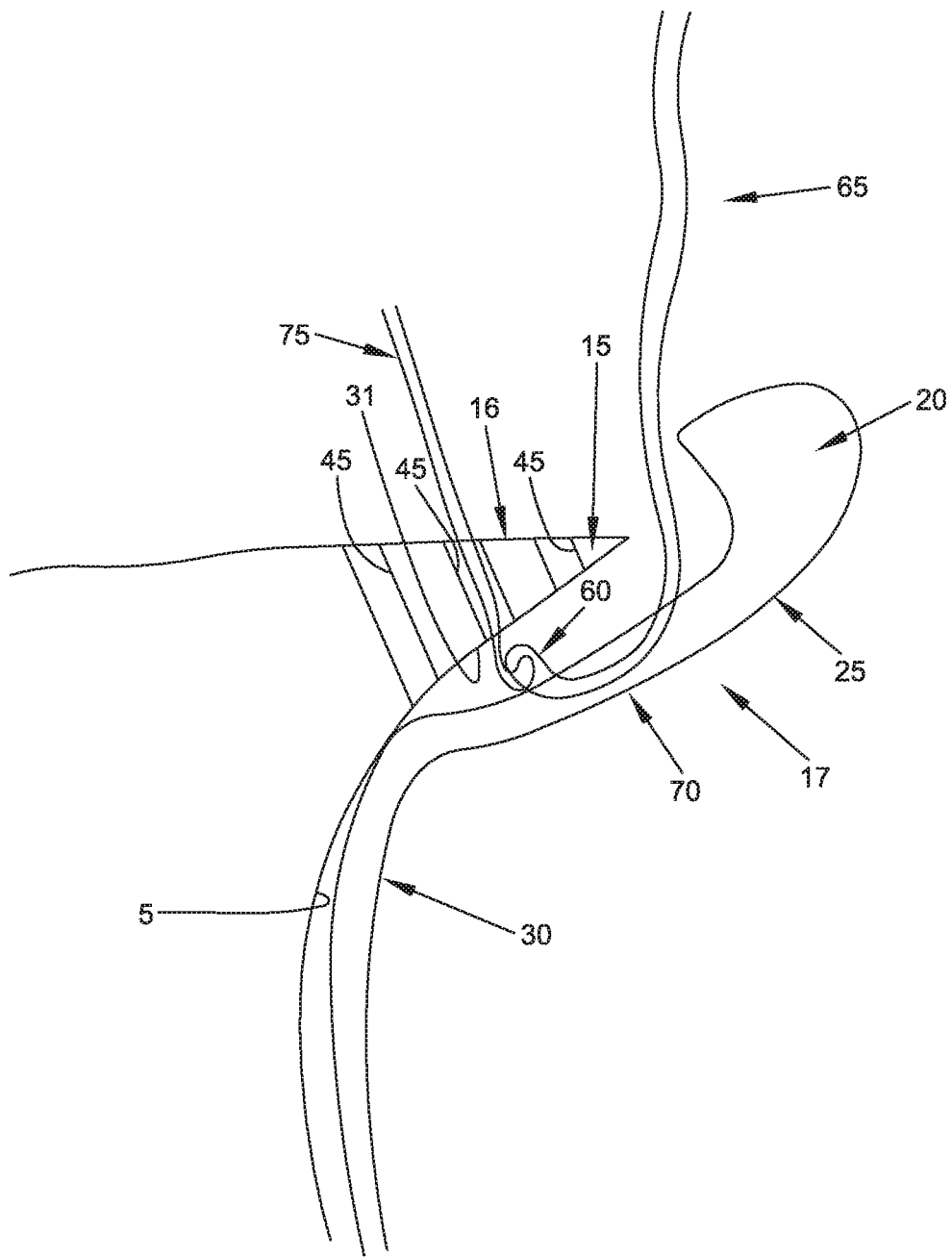
Figure 6:
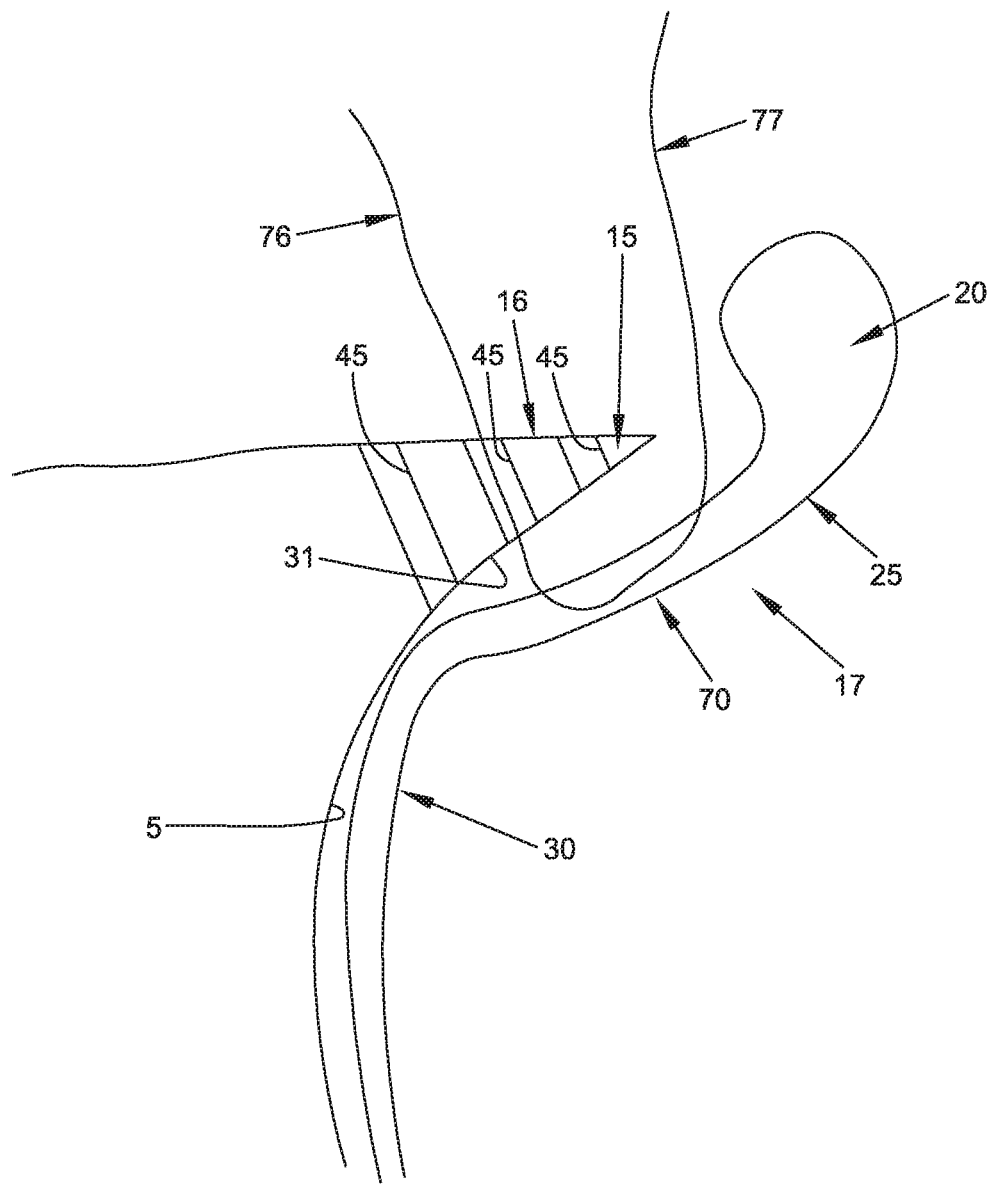

Then, as seen in FIG. 5, a suture retriever 75 is advanced, "outside-in", through a hole 45 formed in rim 15 of acetabular cup 5 (i.e., from acetabular shelf 16 to cortical bone bed 31). Using suture retriever 75, one leg 76 of loop 60 of suture 65 is drawn, "inside-out", through a hole 45 of acetabular cup 5 (i.e., from cortical bed 31 to acetabular shelf 16), in the manner shown in FIG. 6.

If desired, suture retriever 75 may be of the sort disclosed in U.S. Patent Publication No. 2014/0012292. Alternatively, other suture passers of the sort well known in the art may be used.

Figure 7:
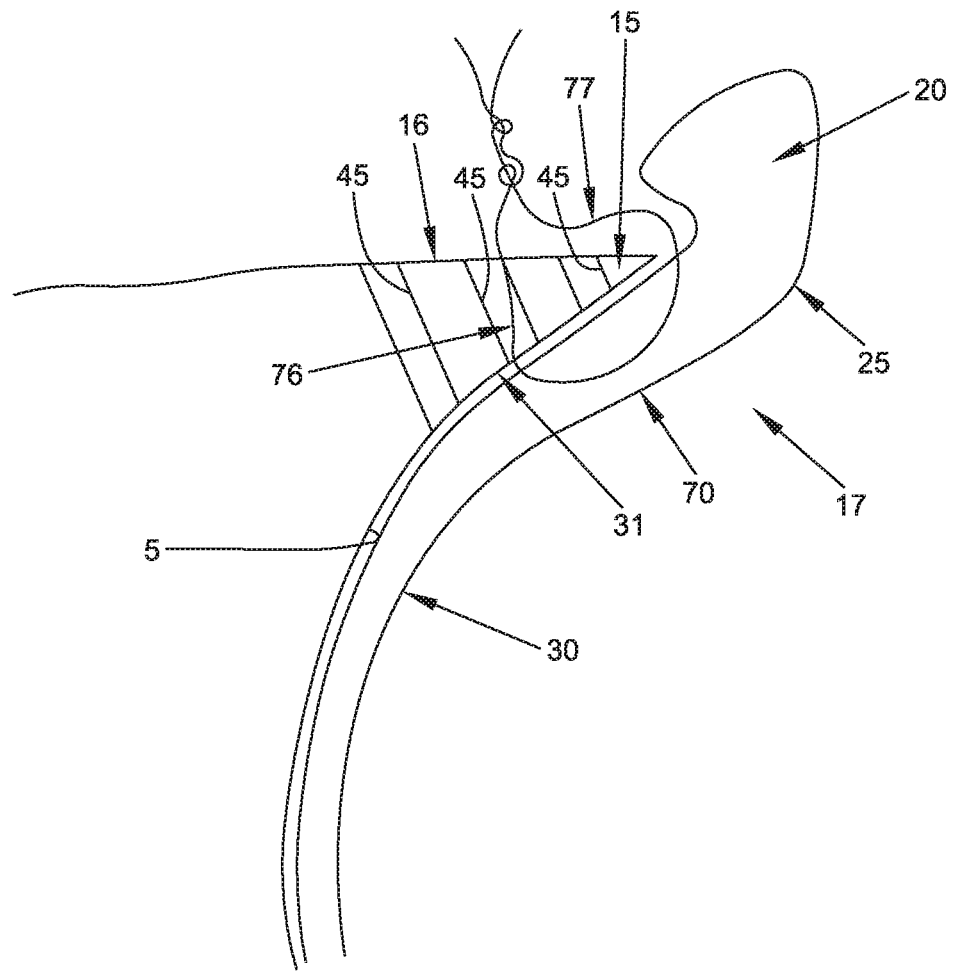

As seen in FIG. 7, the two legs 76, 77 of loop 60 of suture 65 are then knotted on the outside of rim 15 of acetabular cup 5 (e.g., adjacent to acetabular shelf 16), whereby to secure detached tissue 17 in position against cortical bone bed 31. Note that inasmuch as the holes 45 formed in rim 15 of acetabular cup 5 allow blood to be released from the underlying cancellous bone to cortical bone bed 31 (against which detached tissue 17 is re-attached), enhanced tissue re-attachment may be achieved. Furthermore, it should be appreciated that inasmuch as loop 60 of suture 65 is passed through detached tissue 17 so that suture 65 does not extend through articular side 70 of detached tissue 17, femoral head 10 will not be subjected to abrasion during movement due to engagement with suture 65.

Figure 8:
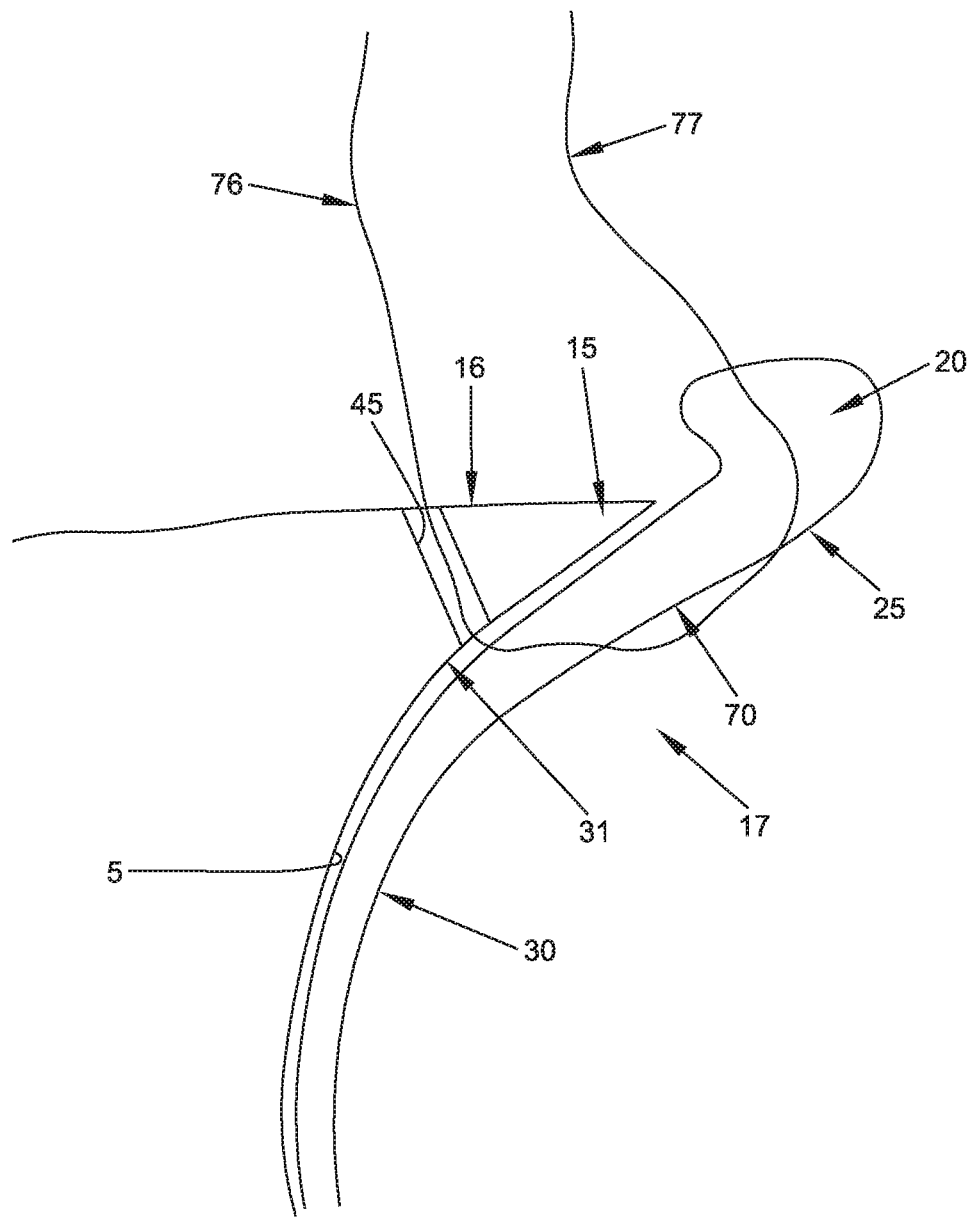
FIGS. 8 and 9 are schematic views showing another approach for providing microfracture therapy to the rim of the acetabular cup and for re-attaching soft tissue to the acetabular cup.
Figure 9:
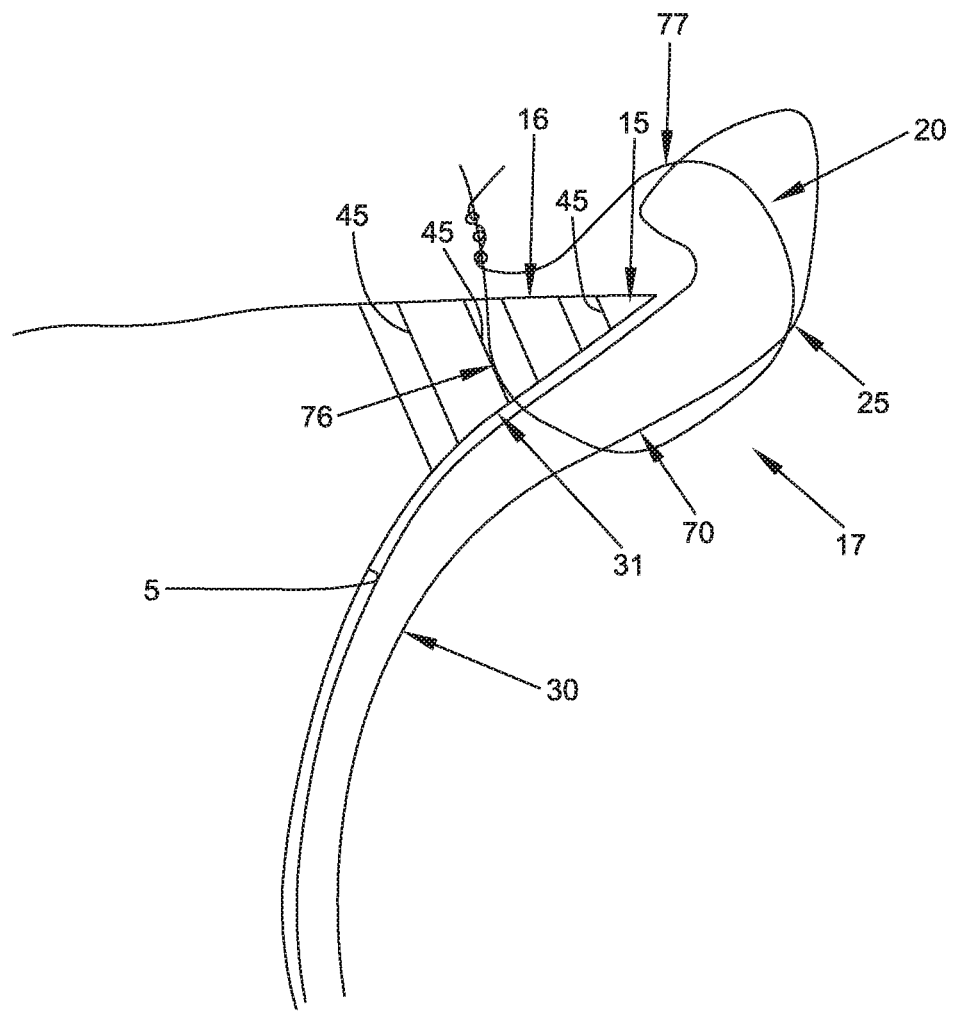
Figure 10:
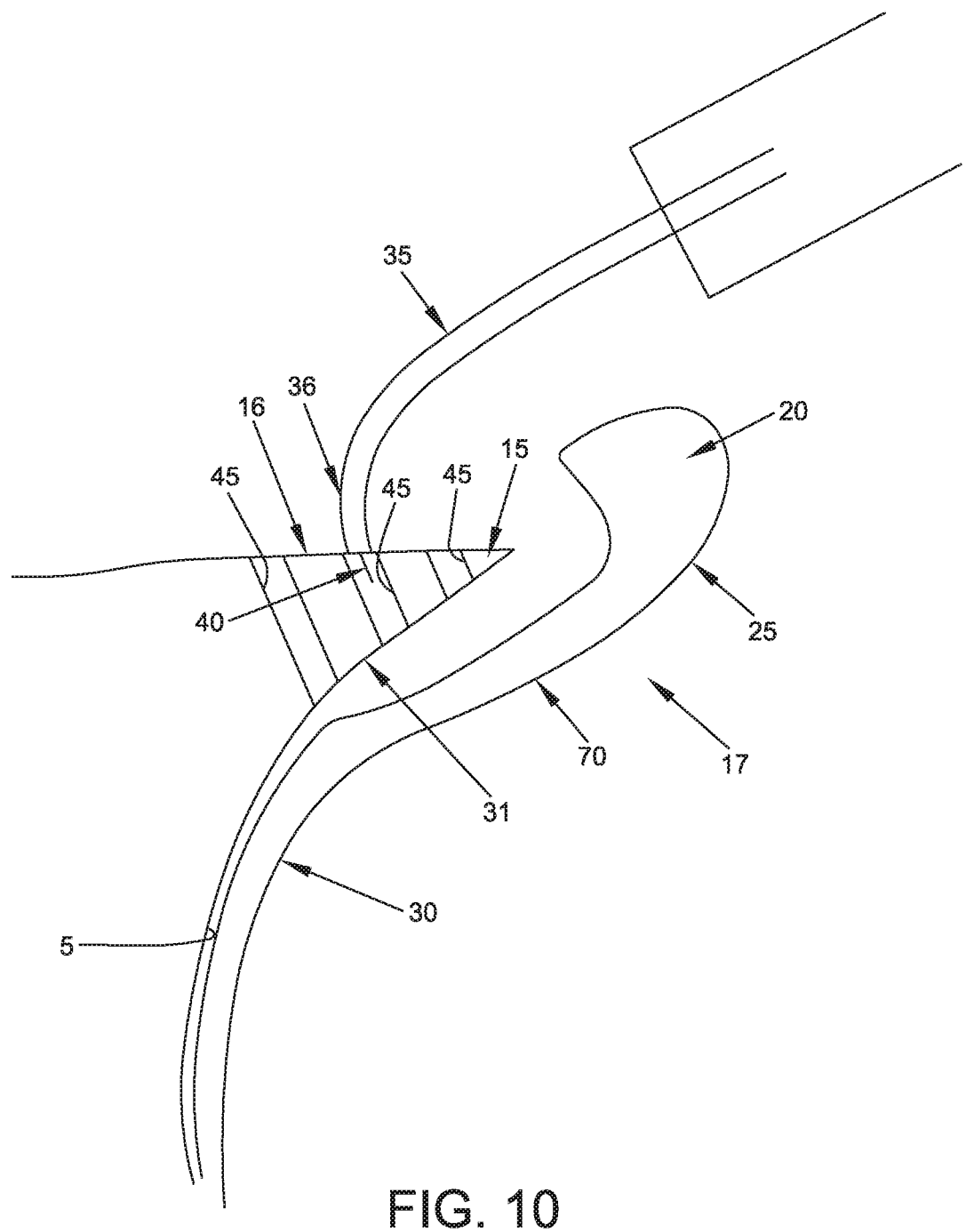
FIGS. 10-17 are schematic views showing still another approach for providing microfracture therapy to the rim of the acetabular cup and for re-attaching soft tissue to the acetabular cup.
Figure 11:
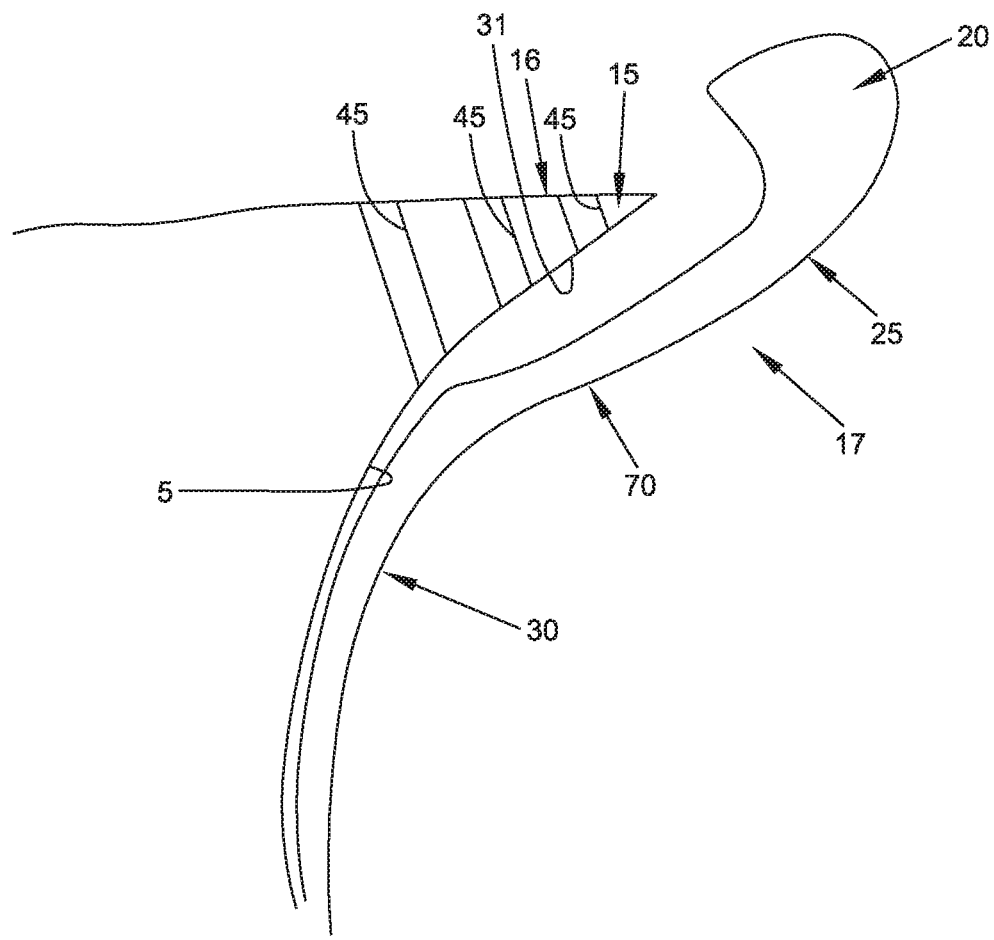
Figure 12:
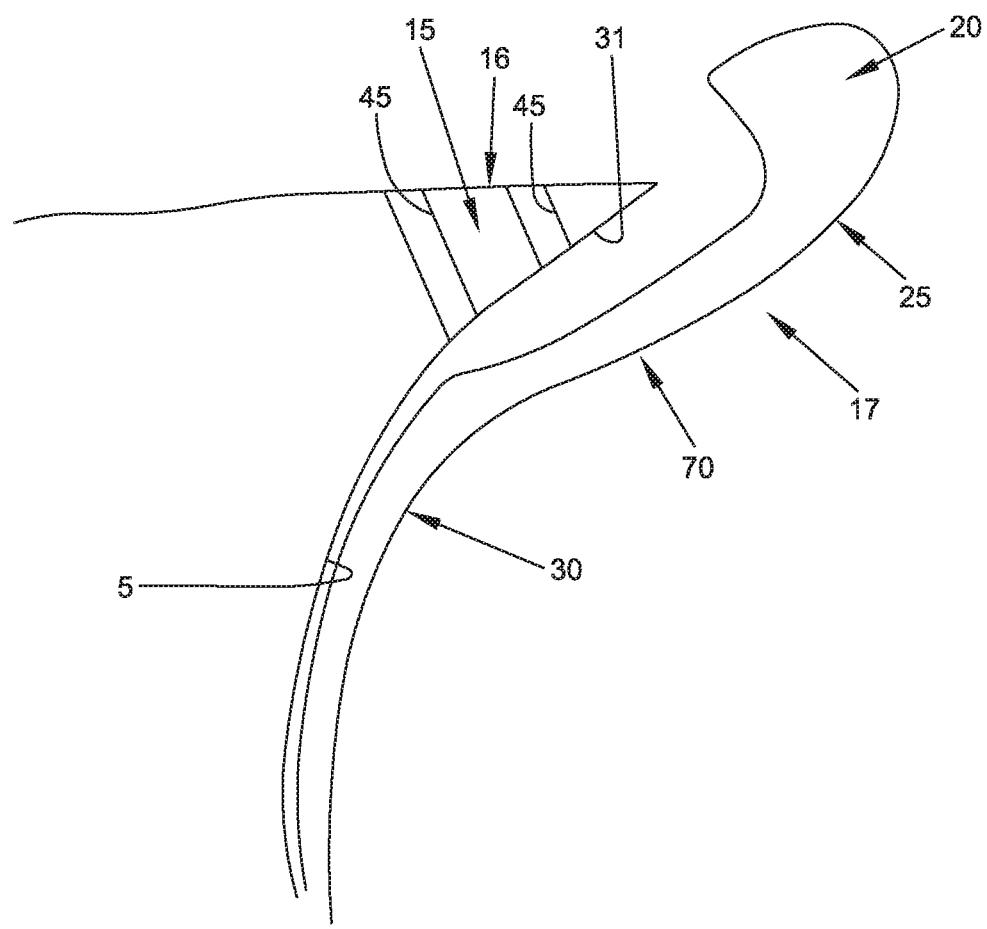

FIGS. 8 and 9 show another form of the present invention. Essentially, the concept shown in FIGS. 8 and 9 is similar to that shown in FIGS. 1-7, except that (i) suture 65 passes completely through detached tissue 17, so as to open on articular side 70 of detached tissue 17, and (ii) suture limb 77 extends through labrum 20, whereby to draw labrum 20 against rim 15 of acetabular cup 5. In one embodiment, suture 65 is bioresorbable. This is advantageous in that once suture 65 degrades it will no longer be a potential source of abrasion against femoral head 10. Suture 65 may comprise a braided or monofilament construction. The size of suture 65 is preferably between #7-0 and #2, and more preferably between #3-0 and #6-0. It will be appreciated that a higher suture tension may cause suture 65 to pull through detached tissue 17; therefore, a light tension is preferably applied to suture 65 so as to secure detached tissue 17 to cortical bone bed 31 without damaging detached tissue 17.

Figure 13:
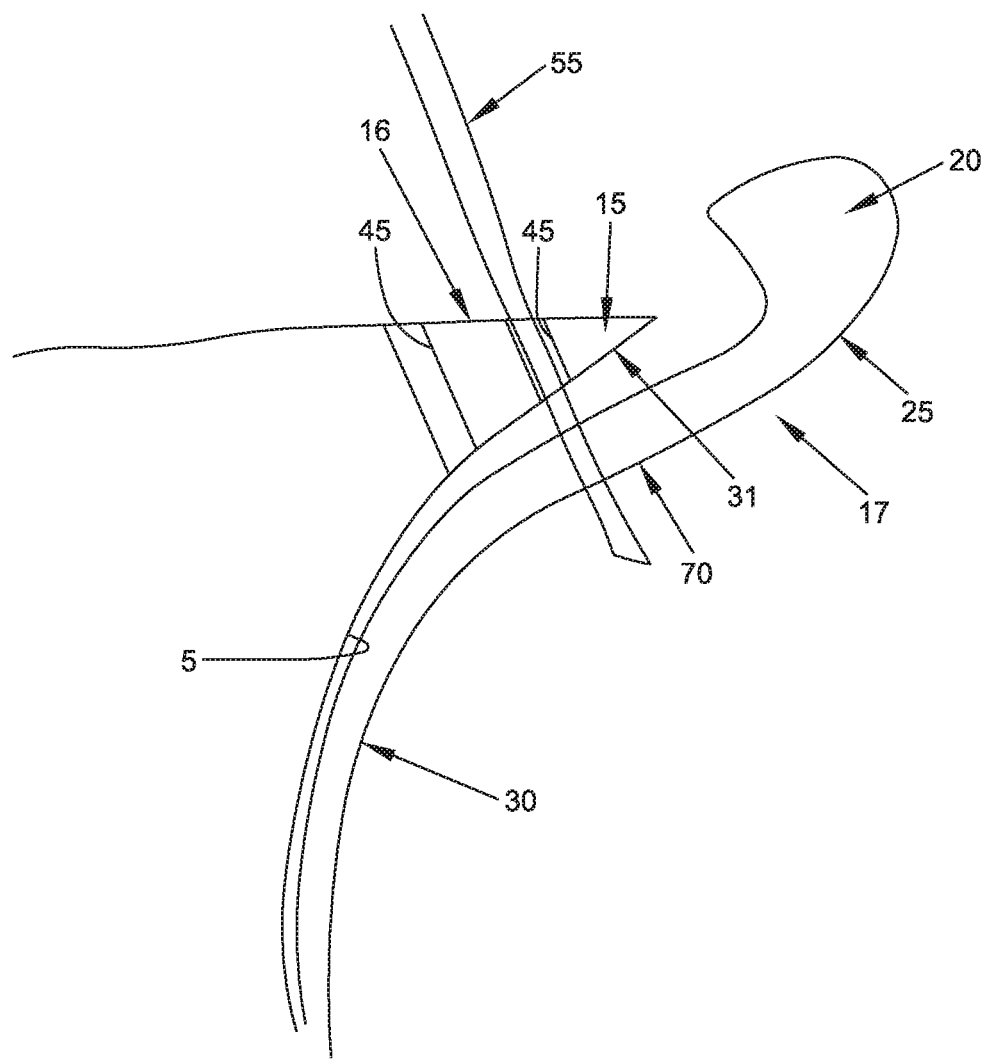
Figure 14:
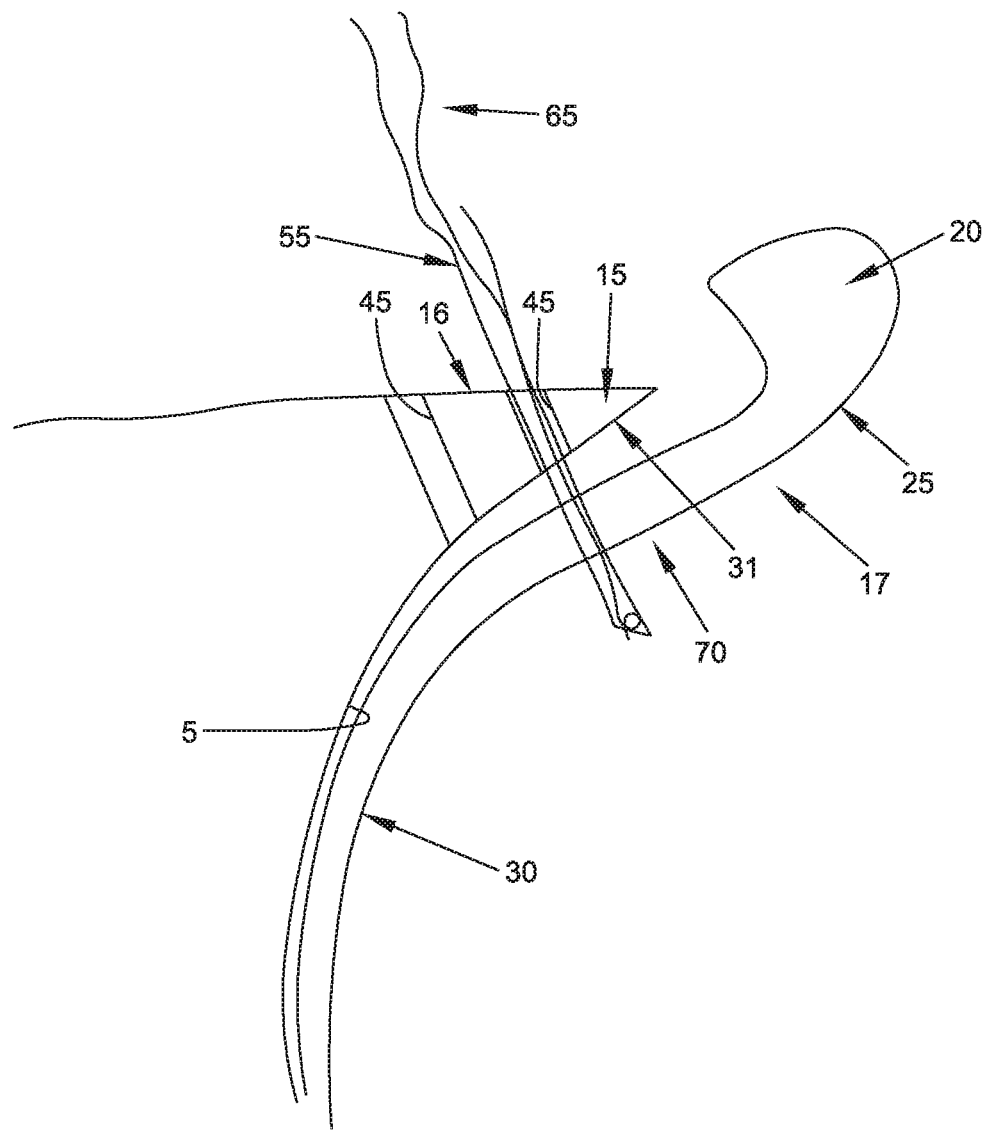
Figure 15:
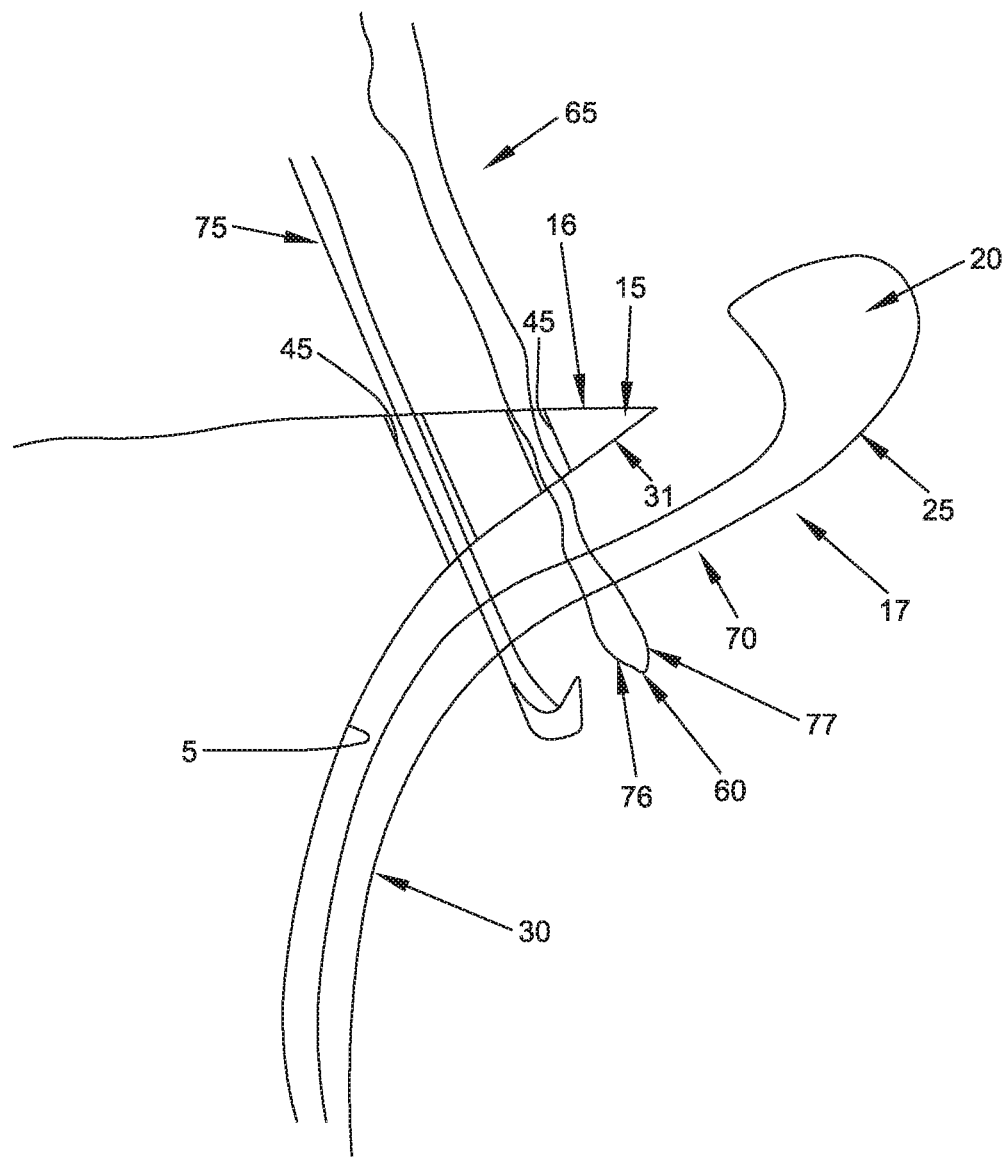
Figure 16:
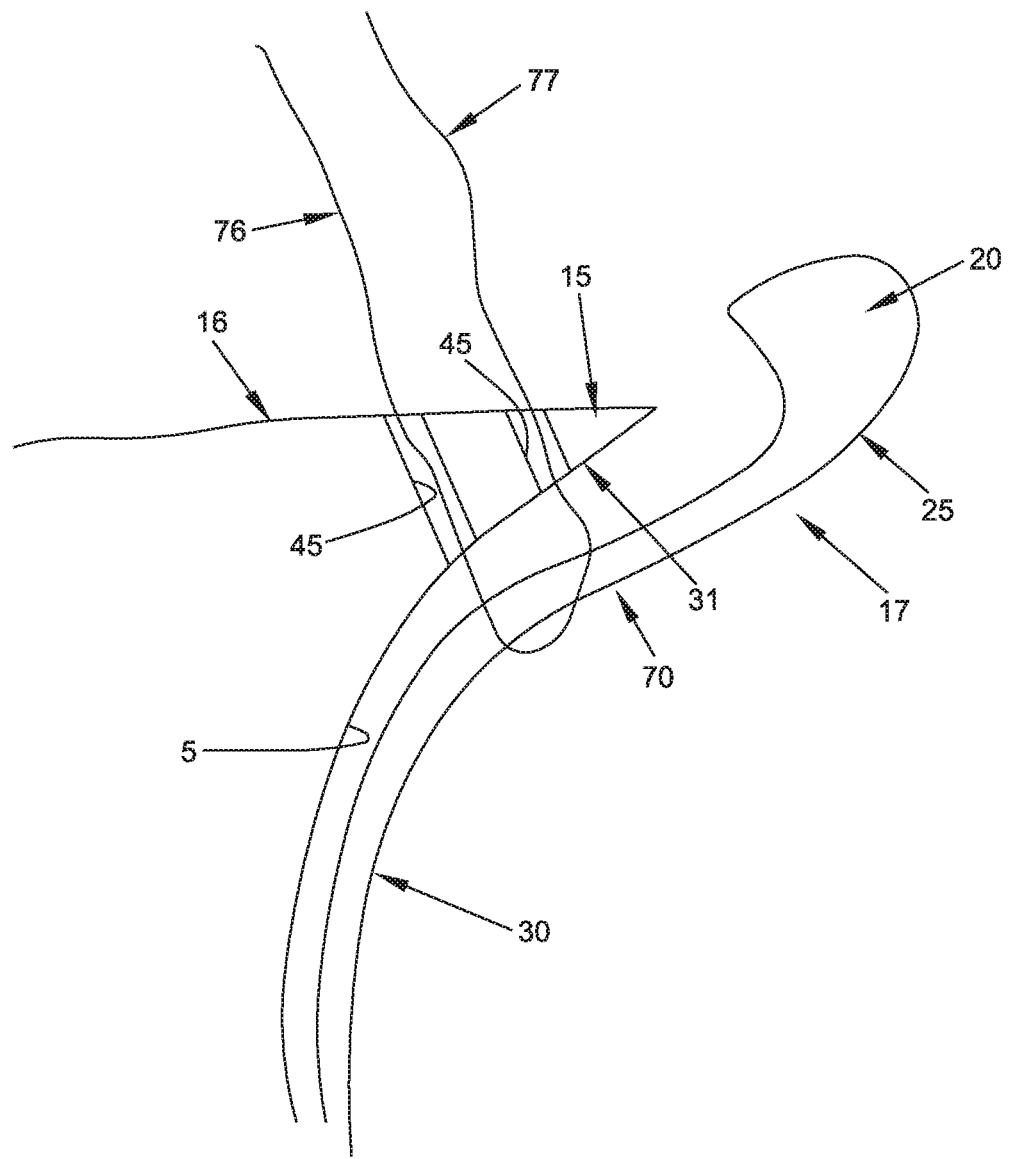
Figure 17:
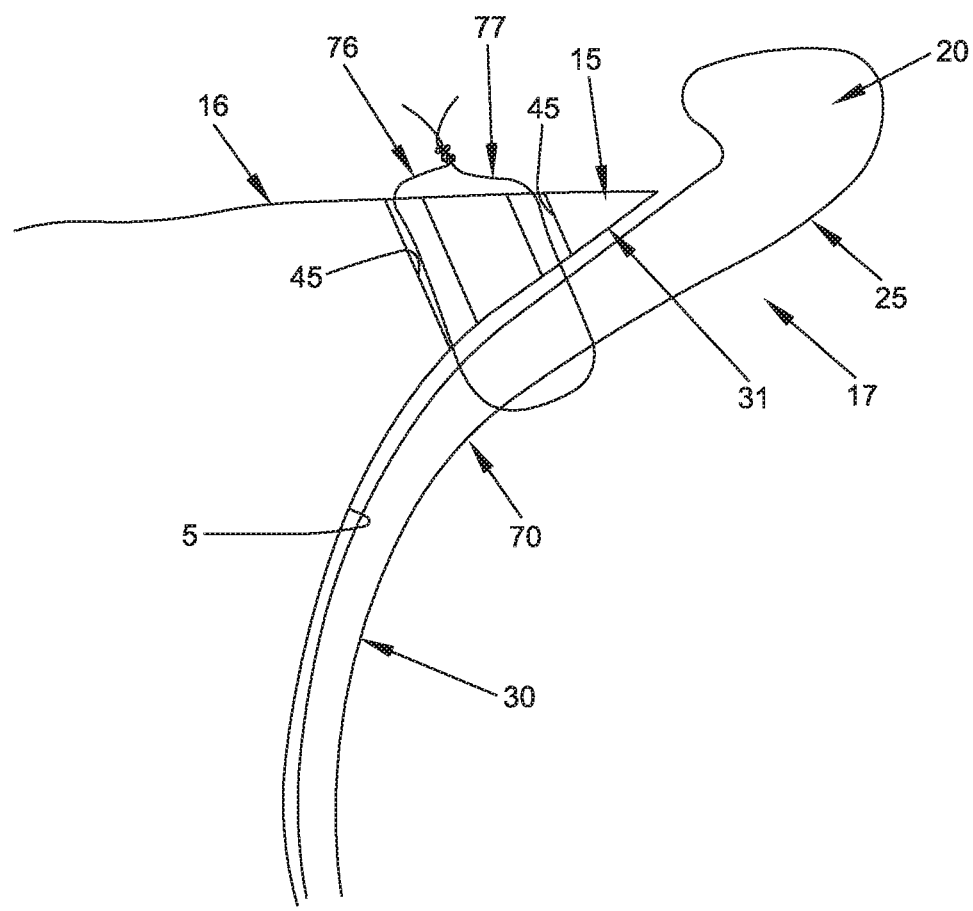

FIGS. 10-17 show another form of the present invention. In this form of the invention, and looking first at FIGS. 10 and 11, curved drill guide 35 and flexible drill bit 40 are used to form multiple holes 45 through rim 15 of acetabular cup 5, advancing with an "outside-in" approach (i.e., from acetabular shelf 16 to cortical bone bed 31). Then detached tissue 17 is moved toward cortical bone bed 31 (FIG. 12) which, as discussed above, is wetted with the blood released from the underlying cancellous bone due to the microfracture therapy provided by bone holes 45. Next, suture passer 55 is advanced through one of the holes 45 in rim 15 of acetabular cup 5 and through detached tissue 17 (FIGS. 13 and 14). Then suture passer 55 is withdrawn, leaving loop 60 of suture 65 on the articular side 70 of detached tissue 17, with suture strands 76, 77 extending back through detached tissue 17 and holes 45 in acetabular rim 15. Next, suture retriever 75 is passed through another of the holes 45 in rim 15 of acetabular cup 5 and through detached tissue 17, and then the suture retriever is used to withdraw one leg 77 of suture loop 60 back to the exterior of rim 15 of acetabular cup 5 (FIGS. 15 and 16). Then the two legs 76, 77 of suture 65 are knotted (e.g., adjacent to acetabular rim 16), whereby to hold detached tissue 17 against rim 15 of acetabular cup 5 (FIG. 17).

Figure 18:
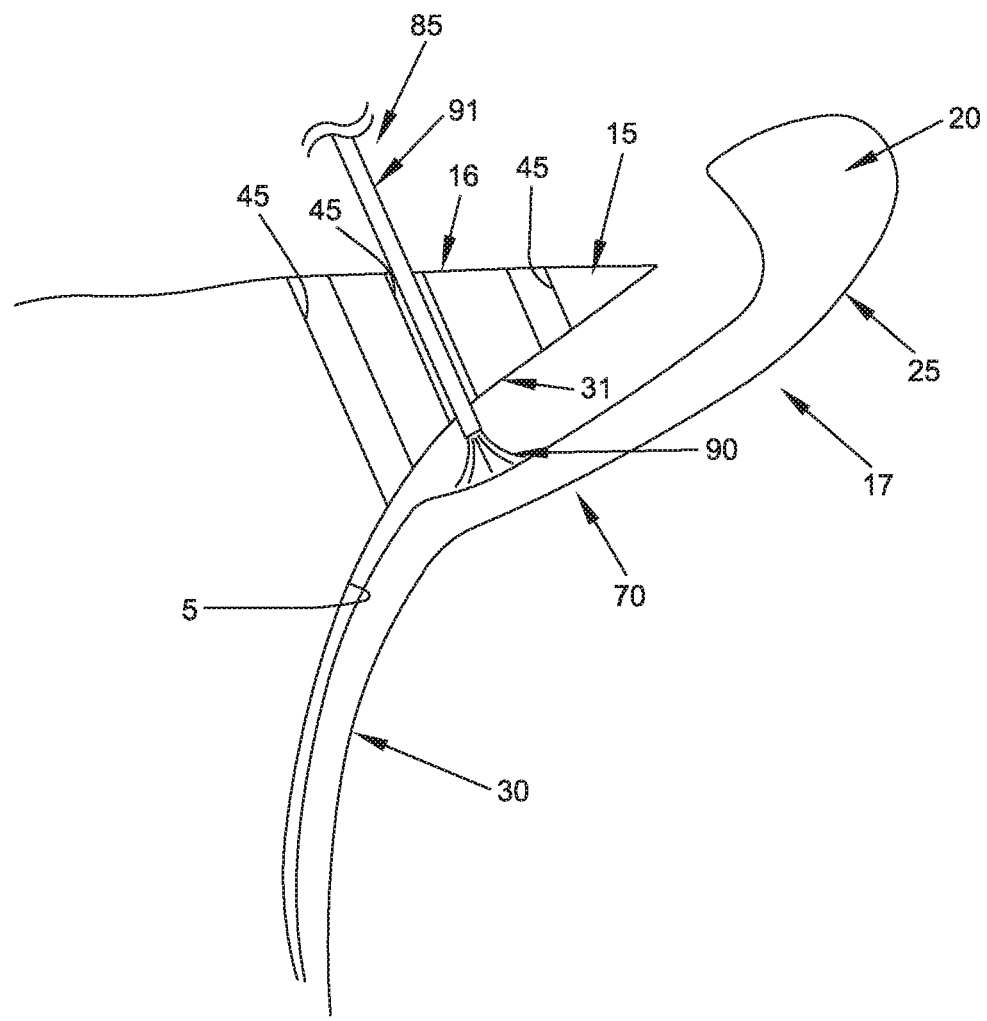
FIG. 18 is a schematic view showing how a biological substance may be disposed between the detached tissue and the cortical bone bed of the acetabular cup.

If desired, the surgeon may use an injection device 85 to inject a biological substance 90 into the space between detached tissue 17 and cortical bone bed 31 of acetabular cup 5. The surgeon can access this space through one of the holes 45 drilled through rim 15 of acetabular cup 5. For example, as shown in FIG. 18, an injection device 85 comprising a shaft 91 is inserted through one of the holes 45 in rim 15 of acetabular cup 5 so that the distal tip of injection device 85 is positioned in the space between detached tissue 17 and cortical bone bed 31 of acetabular cup 5. The biological substance 90 is then injected into the space between detached tissue 17 and cortical bone bed 31 of acetabular cup 5. The injection of biological substance 90 preferably occurs after at least one hole 45 is drilled through rim 15 of acetabular cup 5 and after suture 60 is passed through detached tissue 17, but prior to detached tissue 17 being secured to the bone. Alternatively, the injection of biological substance 90 can occur before suture 60 is passed through detached tissue 17, or after detached tissue 17 is secured to the bone. The biological substance may comprise fibrin glue. Alternatively, the biological substance may comprise platelet rich plasma (PRP), stem cells, cartilage particles (e.g., ACI—Autologous Chondrocyte Implantation, Allograft Chondrocyte Implantation), Bone Morphogenetic Protein 7 (BMP7) also known as Osteogenic Protein-1 (OP-1), or another biological substance which either enables the re-attachment of the detached tissue to the bone and/or generates new cartilage. If desired, pressure can be applied (e.g., with an inflated balloon, a manual instrument, etc.) to the articular side 70 of detached tissue 17 after the biological substance has been injected so as to enhance the distribution and surface contact of biological substance 90.

Figure 19:
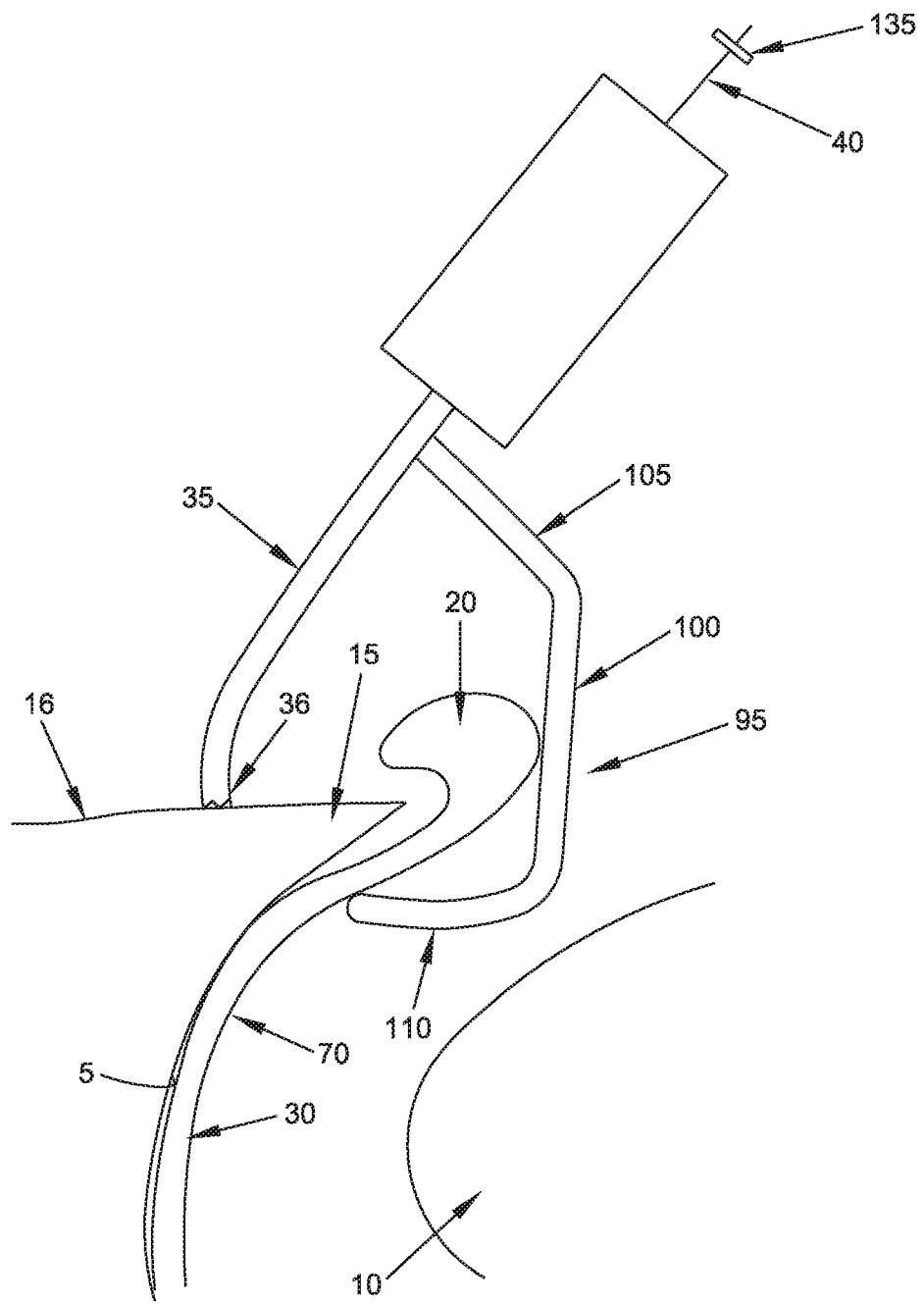
FIGS. 19 and 20 are schematic views showing yet another approach for providing microfracture therapy to the rim of the acetabular cup and for re-attaching soft tissue to the acetabular cup.
Figure 20:
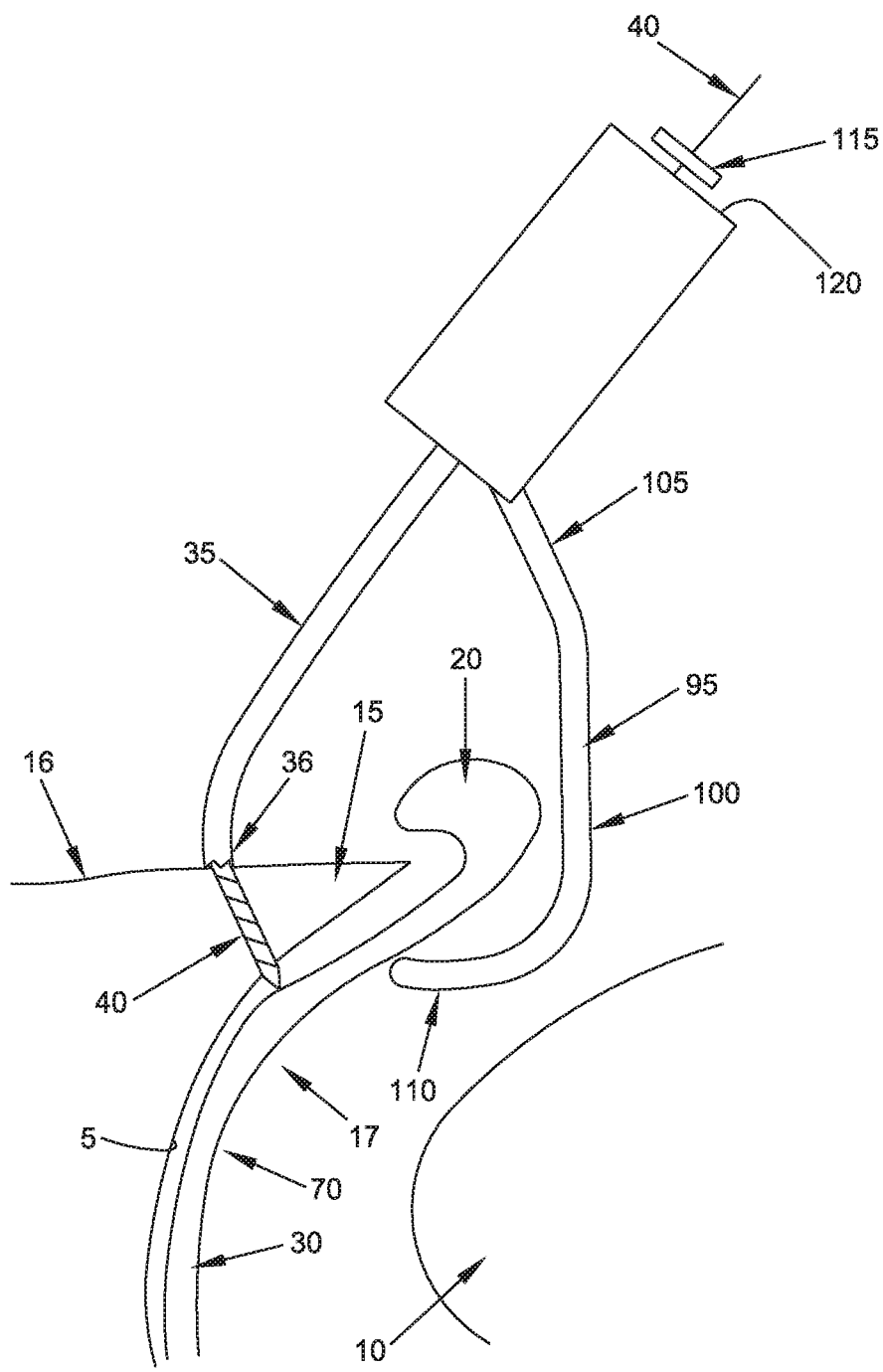

In another form of the invention, and looking now at FIGS. 19 and 20, curved drill guide 35 may include an aiming guide 95 for indicating the location at which flexible drill 40 bit would exit detached tissue 17 if flexible drill bit 40 were to be drilled all the way through detached tissue 17. More particularly, aiming guide 95 comprises an elongated shaft 100 having a proximal end 105 and a distal end 110. Proximal end 105 of aiming guide 95 is secured to curved drill guide 35 so that (i) distal end 110 of aiming guide 95 is substantially aligned with distal end 36 of curved drill guide 35, and (ii) distal end 110 of aiming guide 95 is spaced from distal end 36 of curved drill guide 35. Thus, a gap exists between distal end 110 of aiming guide 95 and distal end 36 of curved drill guide 35. This gap is sized so as to be large enough to accommodate the relevant portion of the acetabulum and any other tissue (e.g., cartilage 30, labrum 20, the "transition zone" 25 between cartilage 30 and labrum 20, etc.) which may be disposed between distal end 36 of curved drill guide 35 and distal end 110 of aiming guide 95 when distal end 36 of curved drill guide 35 is positioned against the acetabulum for drilling through the acetabulum.

In use, curved drill guide 35, with its aiming guide 95 attached, is moved into position so that distal end 36 of curved drill guide 35 approaches the acetabulum and distal end 110 of aiming guide 95 approaches the relevant portion of the acetabulum and any other tissue (e.g., cartilage 30, labrum 20, the "transition zone" 25 between cartilage 30 and labrum 20, etc.) which may be disposed between distal end 36 of curved drill guide 35 and distal end 110 of aiming guide 95. Thus, distal end 36 of curved drill guide 35 will be located in the region of acetabular shelf 36 where flexible drill bit 40 will enter the bone, and distal end 110 of aiming guide 95 will be located on the articular side of the acetabulum and any adjacent tissue (e.g., cartilage 30, labrum 20, the "transition zone" 25 between cartilage 30 and labrum 20, etc.). Distal end 36 of curved drill guide 35 is then advanced to the surface of acetabular shelf 16 while watching the disposition of distal end 110 of aiming guide 95 so as to ensure that the bone hole 45 will be drilled along the desired line. Once distal end 36 of curved drill guide 35 is securely positioned against acetabular shelf 16 and its proper positioning confirmed by observing the position of distal end 110 of aiming guide 95, drilling of bone holes 45 may be appropriately effected.

Preferably flexible drill bit 40 passes completely through the acetabulum but stops short of any other tissue (e.g., cartilage 30, labrum 20, the "transition zone" 25 between cartilage 30 and labrum 20, etc.) which may be disposed on the articular side of the acetabulum. See FIG. 20. This may be accomplished by providing a stop 115 on flexible drill bit 40 (which engages a corresponding portion 120 of curved drill guide 35) so as to limit distal travel of flexible drill bit 40. By way of example but not limitation, research has shown that the tissue on the articular side of the acetabulum (e.g., cartilage 30, labrum 20, the "transition zone" 25 between cartilage 30 and labrum 20, etc.) is approximately 1-3 mm thick in the region where flexible drill bit 35 is to pass through the acetabulum—therefore, stop 115 can be set so as to stop distal movement of flexible drill bit 35 approximately 1-3 mm from distal end 110 of aiming guide 95.

Figure 21:
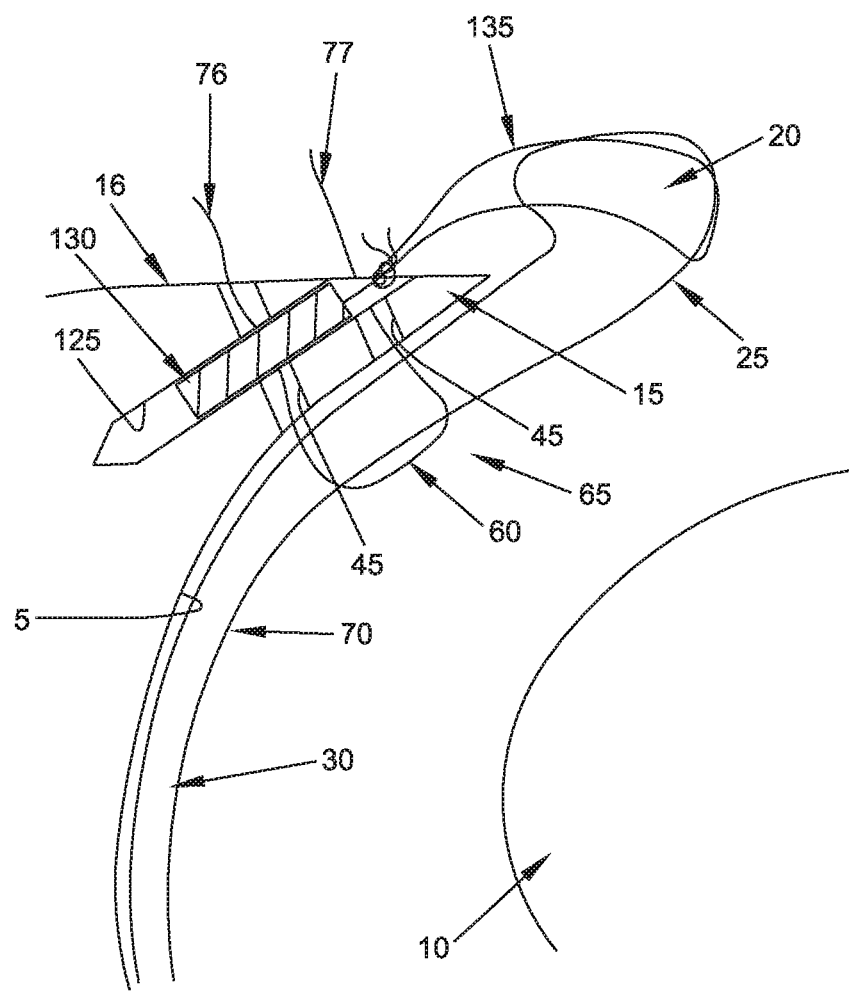
FIG. 21 is a schematic view showing another approach for providing microfracture therapy to the rim of the acetabular cup and for re-attaching soft tissue to the acetabular cup.
Figure 22:
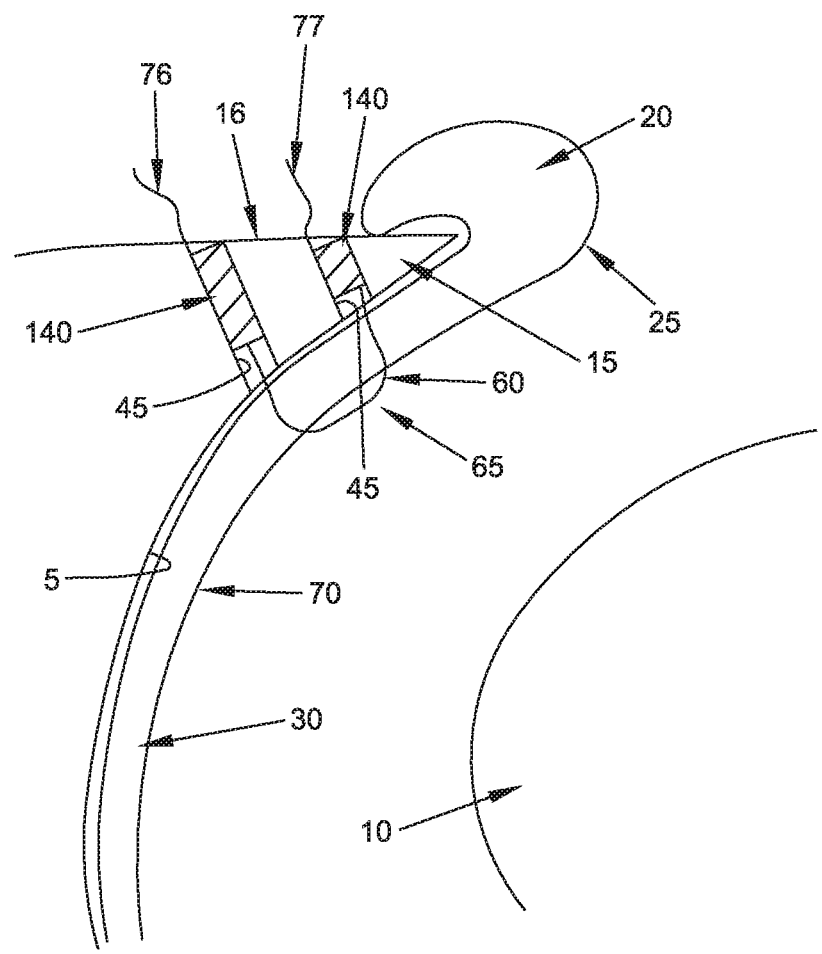
FIG. 22 is a schematic view showing still another approach for providing microfracture therapy to the rim of the acetabular cup and for re-attaching soft tissue to the acetabular cup.

FIGS. 21 and 22 show additional approaches for securing detached tissue 17 (e.g., cartilage 30, labrum 20, the "transition zone" 25 between cartilage 30 and labrum 20, etc.) to the articular side of the acetabulum (i.e., to cortical bone bed 31).

More particularly, in FIG. 21, it will be seen that a length of suture 65 may be passed through one microfracture hole 45, through the detached tissue 17 (e.g., cartilage 30, labrum 20, the "transition zone" 25 between cartilage 30 and labrum 20, etc.), and then back out through another microfracture hole 45. Additionally, an anchor hole 125 may be drilled into the acetabulum and a suture anchor 130 and its associated suture 135 used to draw labrum 20 back onto rim 15 of the acetabulum. Preferably, microfracture holes 45 coincide with suture anchor hole 125 such that suture anchor 130 will additionally secure the suture 65 (which passes through detached tissue 17) to the bone. In other words, the detached tissue repair suture 65 will pass between suture anchor 130 and anchor hole 125 such that suture anchor 130 will secure suture 65 against the side wall of anchor hole 125.

Alternatively, in FIG. 22, it will be seen that a suture 65 may be passed through one microfracture hole 45, through detached tissue 17 (e.g., cartilage 30, labrum 20, the "transition zone" 25 between the cartilage and the labrum, etc.), and then back out through another microfracture hole 45, and then the suture lengths 76, 77 may be made secure in their respective microfracture holes 45 using anchors 140 (e.g., simple interference screw anchors, push-in "plug-type" anchors, etc.).

Since microfracture hole(s) 45 is/are open at both ends (i.e., at acetabular shelf 16 and cortical bone bed 31), it may be desirable to direct the blood flowing from microfracture hole(s) 45 to flow only (or substantially only) towards cortical bone bed 31 (where it is intended to flow for the microfracture benefits described above), and not towards acetabular shelf 16 (where it does not have a benefit, inasmuch as acetabular shelf 16 does not comprise soft tissue). This may be accomplished by placing plugs (e.g., anchors 140) within microfracture hole(s) 45 at (or near to) the end(s) of hole(s) 45, approximate to acetabular shelf 16. Plugging the end(s) of hole(s) 45 may also be accomplished by injecting a material (e.g., fibrin glue) into the acetabular shelf end(s) of hole(s) 45 so as to fill those end(s) of hole(s) 45.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention. By way of example but not limitation, although hole(s) 45 of the "outside-in" microfracture therapy of the present invention has/have been described as being formed using a drilling process (e.g., using curved drill guide 35 and flexible drill bit 40), the "outside-in" hole(s) 45 can be formed by other means, e.g., by impacting the flexible drill bit so as to penetrate the bone, or by impacting another instrument so as to penetrate the bone, etc. Furthermore, if desired, drill guide 35 may not be curved, and/or drill bit 40 may not be flexible. These and other variations of the present invention are considered to be within the spirit and scope of the present invention.

What is claimed is:

1. A method for injecting a biological substance into space between bone and soft tissue, the method comprising:
    forming at least one hole extending from a first side of the bone to a second side of the bone, wherein the second side of the bone comprises a cortical bone bed, wherein the soft tissue is disposed on the second side of the bone, wherein the soft tissue comprises a first region and a second region, wherein the first region of the soft tissue is attached to the second side of the bone, wherein the second region of the soft tissue comprises a first surface and a second surface with the first surface of the second region of the soft tissue facing the cortical bone bed; and
    injecting a biological substance through the at least one hole and directly into the space between the cortical bone bed and the first surface of the second region of the soft tissue so that the biological substance directly contacts the cortical bone bed and the first surface of the second region of the soft tissue.

2. The method according to claim 1 wherein the soft tissue comprises at least one from the group consisting of cartilage, labrum, and a transition zone between cartilage and labrum.

3. The method according to claim 1 further comprising sealing the first side of the bone at the at least one hole.

4. The method according to claim 1 wherein the biological substance comprises one from the group consisting of fibrin glue, platelet rich plasma (PRP), stem cells, cartilage particles and Bone Morphogenetic Protein 7 (BMP7).

5. The method according to claim 1 wherein the biological substance comprises a biological substance which enables at least one of (i) the re-attachment of the second region of the soft tissue to the cortical bone bed, and (ii) generating new cartilage at the second side of the bone.

6. The method according to claim 1 wherein the biological substance is injected through an injection device.

7. The method according to claim 6 wherein the injection device comprises a distal end and a proximal end, and further wherein injecting the biological substance comprises passing the injection device through the at least one hole so that the distal end of the injection device is disposed in the space between the cortical bone bed and the first surface of the second region of the soft tissue.

8. The method according to claim 1 wherein the at least one hole extending from the first side of the bone to the second side of the bone is formed using a drill bit.

9. The method according to claim 8 wherein the drill bit is advanced through a drill guide, wherein the drill guide comprises a distal end through which the drill bit emerges, and the drill guide further comprises an aiming guide having a distal end aligned with, but spaced from, the distal end of the drill guide.

10. The method according to claim 1 wherein the at least one hole is formed using an outside-in approach.

11. The method according to claim 1 further comprising attaching the second region of the soft tissue to the second side of the bone at the cortical bone bed.

12. The method according to claim 11 wherein the biological substance is injected after attaching the second region of the soft tissue to the second side of the bone.

13. The method according to claim 11 wherein the biological substance is injected before attaching the second region of the soft tissue to the second side of the bone.

14. The method according to claim 11 wherein the second region of the soft tissue is attached to the cortical bone bed using suture.

15. The method according to claim 14 wherein the suture comprises a first leg, a second leg and an intermediate portion connecting the first leg to the second leg, and further wherein the first leg of the suture extends from the first side of the bone to the cortical bone bed through a first hole, the intermediate portion of the suture extends through the soft tissue, and the second leg of the suture extends from the cortical bone bed to the first side of the bone through a second hole.

16. The method according to claim 15 wherein the first leg of the suture and the intermediate portion of the suture are advanced through the first hole and through the soft tissue using an outside-in approach, and further wherein the second leg of the suture is advanced through the soft tissue and through the second hole using an inside-out approach.

17. The method according to claim 15 wherein the first leg of the suture is secured to the second leg of the suture adjacent the first side of the bone.

18. The method according to claim 17 wherein the first leg of the suture is secured to the second leg of the suture with a knot.

19. The method according to claim 15 wherein the first and second legs of the suture are secured to the first side of the bone using at least one anchor.

20. The method according to claim 19 wherein the at least one anchor comprises a second suture secured to the soft tissue of the patient.

21. The method according to claim 15 wherein the first leg of the suture is secured in the first hole using a first anchor and the second leg of the suture is secured in the second hole using a second anchor.

22. The method according to claim 14 wherein the suture does not open on an articular side of the soft tissue.

23. The method according to claim 14 wherein the suture opens on an articular side of the soft tissue.

24. The method according to claim 14 wherein the suture does not pass through a labrum of the patient.

25. The method according to claim 14 wherein the suture passes through a labrum of the patient.

26. The method according to claim 1 wherein the first side of the bone comprises an acetabular shelf.

27. A method for injecting a biological substance into space between bone and soft tissue, the method comprising:
    forming at least one hole extending from a first side of the bone to a second side of the bone, wherein the second side of the bone comprises a cortical bone bed, wherein the soft tissue is disposed on the second side of the bone, and further wherein the soft tissue comprises a first region and a second region, wherein the first region of the soft tissue is attached to the second side of the bone, wherein the second region of the soft tissue comprises a first surface and a second surface so that the biological substance directly contacts the cortical bone bed and the first surface of the second region of the soft tissue; and
    injecting a biological substance through the at least one hole and directly into the space between the cortical bone bed and the first surface of the second region of the soft tissue;
    wherein the biological substance enables generating new cartilage at the second side of the bone.

28. The method according to claim 27 wherein generating new cartilage at the second side of the bone causes at least a portion of the second region of the soft tissue to be re-attached to the second side of the bone.

29. The method according to claim 27 wherein the biological substance comprises one from the group consisting of platelet rich plasma (PRP), stem cells, cartilage particles and Bone Morphogenetic Protein 7 (BMP7).

* * * * *